United States Patent [19]
Mulier et al.

[11] Patent Number: 5,405,376
[45] Date of Patent: Apr. 11, 1995

[54] METHOD AND APPARATUS FOR ABLATION

[75] Inventors: Peter M. J. Mulier, St. Paul; Michael F. Hoey, Shoreview, both of Minn.

[73] Assignee: Medtronic, Inc., Minneapolis, Minn.

[21] Appl. No.: 113,541

[22] Filed: Aug. 27, 1993

[51] Int. Cl.$^6$ ............................................. A61M 25/14
[52] U.S. Cl. .................................. 607/127; 607/122; 607/120; 604/131; 604/272
[58] Field of Search ................. 604/23, 26, 280, 264, 604/272, 131; 606/33, 41, 50; 607/113, 134, 154, 105, 122, 120, 127

[56] References Cited

U.S. PATENT DOCUMENTS

| | | |
|---|---|---|
| 5,002,067 | 3/1991 | Berthelsen et al. |
| 5,030,204 | 7/1991 | Badger. |
| 5,060,660 | 10/1991 | Gambale. |
| 5,104,393 | 4/1992 | Isner. |
| 5,165,421 | 11/1992 | Fleischhacker. |
| 5,261,889 | 11/1993 | Laine et al. ............ 604/272 |
| 5,324,325 | 6/1994 | Moaddeb. |

FOREIGN PATENT DOCUMENTS

93/0472  3/1993  WIPO.

OTHER PUBLICATIONS

U.S. Statutory Invention Registration H356, Pub. Nov 3, 1987 Sekes et al.

"Transcoronary Chemical Ablation of Arrhythmias", by Nellens et al., PACE, vol. 15, pp. 1368–1373, Sep., 1992.

"Chemical Ablation by Subendocardial Injection of Ethanol, via Catheter-Preliminary Results in the Pig Heart", Weismuller et al., European Heart Journal, vol. 12, pp. 1234–1239, 1991.

Primary Examiner—C. Fred Rosenbaum
Assistant Examiner—Perry E. Van Over
Attorney, Agent, or Firm—Reed A. Duthler; Harold R. Patton

[57] ABSTRACT

An ablation catheter and a method of performing cardiac ablation using alcohol or other ablating agents. The catheter is provided with a helical hollow needle, which is screwed into heart tissue, after which the ablating agent is delivered through the needle. Prior to ablation, the catheter may be employed to locate an appropriate ablation site or to assess the suitability of an identified ablation site by injection of a exitability reducing agent such as lidocaine, through the hollow needle, followed by a determination of whether the arrhythmia intended to be treated as temporarily terminated.

29 Claims, 3 Drawing Sheets

METHOD AND APPARATUS FOR ABLATION

BACKGROUND OF THE INVENTION

This invention relates generally to the field of devices for cardiac surgery, and more specifically to devices for chemical ablation of cardiac tissue.

The present invention is directed toward treatment of tachyarrhythmias, which are heart rhythms in which an chamber or chamber of the heart exhibits an excessively fast rhythm. In particular, the present invention is directed toward treatment of tachycardias, which are due to the presence of ectopic foci within the cardiac tissue or due to the presence of aberrant condition pathways within the cardiac tissue.

Injection of alcohol into heart tissue has been employed to ablate cardiac tissue. Alcohol may be delivered to blood vessels supplying the tissue to be ablated, as described in "Transcoronary Chemical Ablation of Arrhythmias", by Nellens et al, Pace Vol. 15, pages 1368-1373, September 1992. Alternatively, alcohol can be delivered directly to the tissue to be ablated by means of a needle inserted through a catheter, as described in "Chemical Ablation by Subendocardial Injection of Ethanol via Catheter—Preliminary Results in the Pig Heart", by Weismuller et al, European Heart Journal, Volume 12, pages 1234-1239, 1991.

SUMMARY OF THE INVENTION

The present invention is directed toward improving the consistency and efficacy of chemical ablation, and to increase the overall size and extent of the lesions induced by chemical ablation. These goals are pursued by means of an ablation catheter employing a helical needle intended to be screwed into the myocardium at the site intended for ablation. The helical needle serves to stabilize the location of the catheter during the application of the alcohol or other chemical ablation fluid. In addition, the helical shape of the needle prevents the application of alcohol through the needle from causing the needle to be backed out of its insertion site due to hydraulic pressure, as might occur if a straight, hollow needle were employed. The elongated path defined by the helical needle also reduces the possibility of leakage along the needle and out of the heart tissue. In addition, there is essentially no bleeding following removal of the helical needle, so it can safely be placed in multiple locations for mapping and ablation purposes.

The needle is electrically coupled to a connector on the proximal end of the catheter so that it may be employed for ECG monitoring or cardiac pacing. This feature allows the catheter to be employed to pre-test the identified ablation site by injection of an agent that reduces electrical excitability and thereafter monitoring the ECG via the needle to determine if the arrhythmia has been temporarily terminated. If so, injection of alcohol or other ablating agent follows to accomplish ablation. Otherwise, a new site may be located and pre-tested in the same fashion. Alternatively, the distance from the needle to the desired ablation site may be estimated by injecting known amounts of the excitability reducing agent and determining how much of the agent is required to temporarily terminate the arrhythmia. This information may be used to specify the dosage of alcohol or other ablating agent delivered or may assist in relocating the needle.

DETAILED DESCRIPTION OF THE PREFERRED EMBODIMENTS

Figure 1:
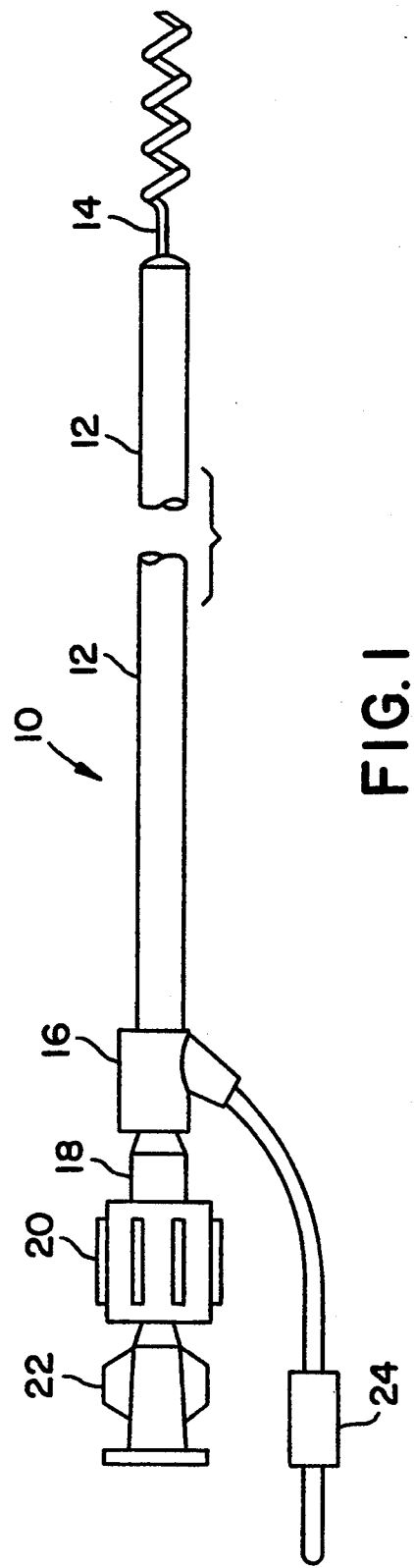
FIG. 1 is a plan view of a catheter adapted to perform the improved method of R-F ablation, according to the present invention.

FIG. 1 is a plan view of a catheter specifically designed for performing chemical ablation according to the present invention. The catheter includes an elongated catheter body 10, comprising an insulative outer sheath 12, which may be made of polyurethane, teflon, or other biocompatible plastic. A hollow, helical needle 14 is located at the distal end of the catheter and is coupled to the distal end of an internal tube, running the length of the catheter. At the proximal end of the catheter a fitting 16 is located, to which luer lock 18 is coupled. Luer lock 18 is coupled to the proximal end of the internal tube. A swivel mount 20 is mounted to luer lock 18, allowing rotation of the catheter relative to luer lock 22. Luer lock 22 is intended to be coupled to a source of alcohol or other ablation fluid. An electrical connector 24 exits fitting 16, and is coupled to needle 14, allowing for the use of needle 14 for functions such as measurement of electrograms within the heart and pacing of heart tissue by application of low energy pulses appropriate for cardiac pacing.

In use, the catheter is advanced to the desired site for ablation, which may have been previously identified by means of cardiac mapping in a fashion similar to cardiac mapping presently employed with R-F ablation procedures. The catheter may be guided to the desired location by being passed down a steerable or guidable catheter, for example, as disclosed in U.S. Pat. No. 5,030,204, issued to Badger et al., or by means of a fixed configuration guide catheter, for example in U.S. Pat. No. 5,104,393, issued to Isner, both of which patents are incorporated herein by reference in their entireties. Alternatively, the catheter may be advanced to the desired site within a heart by means of a deflectable styler, as disclosed in PCT Patent Application Publication No. WO 93/04724, published Mar. 18, 1993, or a deflectable guidewire as disclosed in U.S. Pat. No. 5,060,660, issued to Gambale, et al., both of which patents are incorporated herein by reference in their entireties. When the hollow needle 14 is located at the desired location it is screwed into heart tissue by rotating the catheter body. A torque cable within the catheter body provides for 1:1 torque transfer from the proximal end of the catheter to the hollow needle 14.

When advanced to the desired location, luer lock 22 may optionally be coupled to a pressurized source of an agent such as lidocaine or esmolol which reduces electrical excitability of the heart tissue. An appropriate injection apparatus is discussed in more detail in conjunction with FIG. 6 below. The excitability reducing agent is delivered and the electrical connector is coupled to an ECG machine, allowing the effects of the anesthetic on heart rhythm to be monitored. If the excitability reducing agent is effective to terminate the ectopic activity or interrupt the reentrant pathway associated with the arrhythmia, the site is determined to be appropriate for ablation. If not, the catheter may be relocated and the excitability reducing agent is injected into the new site.

Alternatively, the distance from the needle to the optimum ablation site may be estimated by injecting known amounts of the excitability reducing agent and determining how much of the agent is required to temporarily terminate the arrhythmia. The greater the amount of the agent required, the further the needle is from the optimum ablation site. If the amount of the agent required to terminate the arrhythmia is less than a preset amount, alcohol or another ablation agent such as formaldehyde may be injected, in a dosage based upon the amount of the excitability reducing agent required. If the amount of excitability reducing agent required to terminate the arrhythmia is excessive, this information may still assist in relocating the needle in a subsequent attempt to identify an appropriate ablation site.

After the ablation site has been identified luer lock 22 is coupled to a source of pressurized alcohol. The alcohol is preferably delivered quickly, for example 0.5 cc of ethanol delivered in 4 seconds has been effective in animal testing. Again, the apparatus of FIG. 6 may be employed to deliver the ablation fluid. During delivery of the ablation fluid, the proximal end of the catheter is held to prevent it from rotating, to maintain the hollow needle 14 in its desired location.

The helical configuration of needle 14 is believed to be particularly beneficial in the context of a chemical ablation catheter. Rapid injection of alcohol through a catheter as illustrated requires high pressure (e.g. 400 psi at the catheter entry point), and if a straight needle were to be employed, the possibility that the injected alcohol would act to push the needle out of the tissue hydraulically arises. Because the helical needle must be rotated out of tissue to be removed, and because the catheter includes a torque cable which prevents any substantial twisting of the catheter along its length, this problem can be avoided. Further, because the coiled needle is substantially longer than a corresponding straight needle inserted to the same depth, the injected fluid must travel along a longer path to escape the tissue by backflow along the needle. As noted above, the helical configuration of the needle also essentially eliminates bleeding at the insertion site.

After ablation, the needle 14 may be coupled to a cardiac pacemaker, and cardiac pacing energy may be delivered to the lesion site in an attempt to measure the pacing threshold. The inventors believe that the higher the pacing threshold, the higher local impedance, and, assuming a relatively homogenous lesion, the greater lesion size. As such, the needle 14 can be used to derive a rough estimate of overall lesion size. The needle 14 may also be coupled EKG monitoring equipment to assist in determining whether the tachycardia persists and whether the tissue in the vicinity of the electrode is still participating in aberrant conduction or ectopic activity, associated with the tachycardia.

Figure 2:
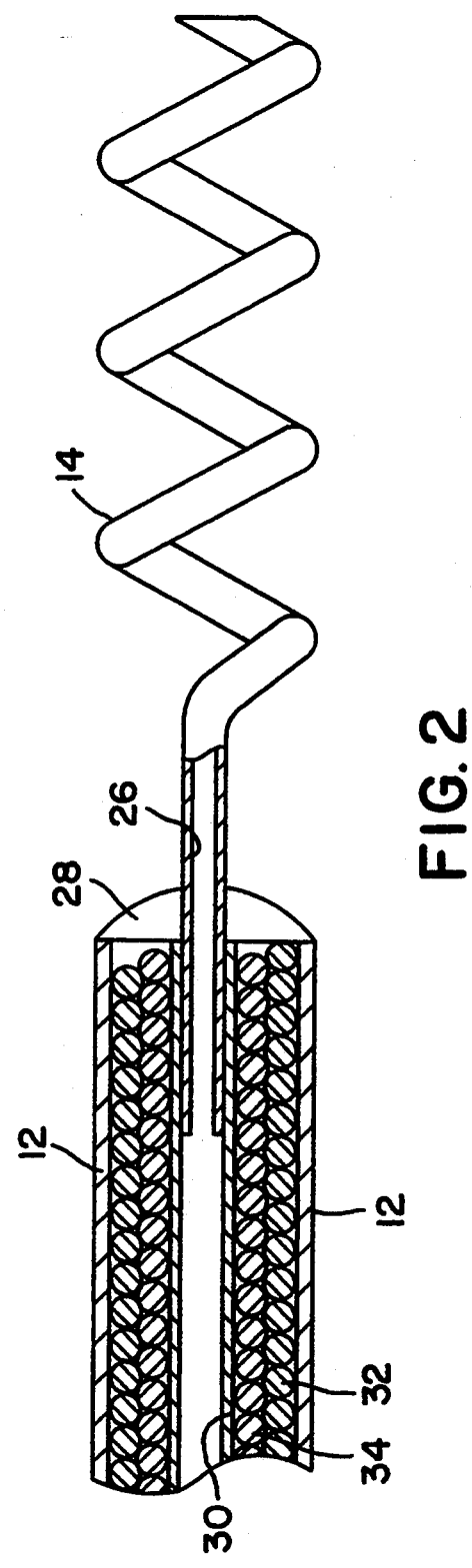
FIG. 2 is a cutaway view through the distal end of the catheter illustrated in FIG. 1.

FIG. 2 illustrates a cutaway version through the end of the catheter illustrated in FIG. 1. In this view, it can be seen that helical needle 14 is provided with an internal lumen 26 which is in communication with the internal lumen of a tube 30. Tube 30 extends to the proximal end of the catheter and is in full communication with luer lock 18, as discussed above, tube 30 may be fabricated of polyimide tubing or of stainless steel tubing. In the present invention, the stainless steel tubing serves as an additional conductor, coupling electrode 14 to electrical connector 24. The use of polyimide tubing, while reducing the overall conductivity of the catheter enhances the flexibility somewhat, and may be beneficial in some cases. In the event that polyimide tubing is employed, it is recommended to apply a steady flow of Ringer's solution through the polyimide tubing to electrode 14 during passage catheter through the vascular system to the ablation site, if possible. The flow of Ringer's solution in this case assists in maintaining the patency of the lumen of tubing 30, as the catheter is advanced through the bloodstream and also prevents plugging of the fluid exit ports on the needle as it enters the cardiac tissue. The apparatus of FIG. 6 provides an appropriate mechanism for delivery if Ringer's solution if necessary.

Surrounding tube 30 are two coils 32 and 34, which are wound in opposite directions, to provide a torque cable. In the case of the specific devices employed by the inventors, a torque cable as manufactured by Lake Region Manufacturing Company of Chaska, Minn. was employed, which torque cable is described in U.S. Pat. No. 5,165,421, incorporated herein by reference in its entirety. Coils 32 and 34 also serve as conductors. As illustrated, tubing 30 is between metal coils 32 and 34 and helical needle 14. However, if polyimide tubing is used, the coils 32 and 34 will serve as the only conductor and thus will be electrically coupled to needle 14 by means of welding, soldering or mechanical interconnection. Insulative sleeve 12 serves both to provide a smooth exterior for the catheter and to insulate the metal coils 32 and 34, along the length of the catheter.

Figure 3:
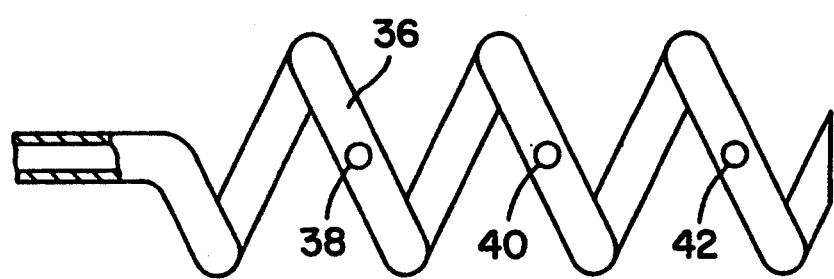
FIGS. 3 and 4 illustrate alternative embodiments of the helical electrode of the catheter illustrated in FIGS. 1 and 2.
Figure 4:
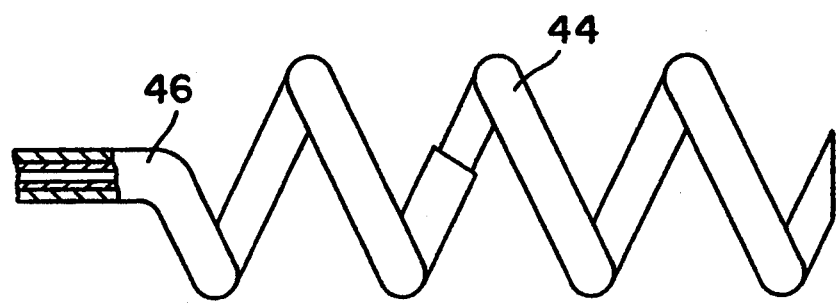

FIGS. 3 and 4 illustrate alternate embodiments of the helical needle illustrated in FIG. 2. The needle 14 in FIG. 2 comprises a hollow tube having a single exit port located as its distal end. Needle 36, illustrated in FIG. 3, corresponds to needle 14 with the exception that additional exit ports 38, 40 and 42 have been added, allowing for dispensing of the alcohol along the length of the helix, to facilitate a wider distribution of alcohol and to increase the size of the lesion produced. Ports 38, 40 and 42 may be laser drilled, and may be spaced in any desired fashion around the circumference of needle 36 and along the length of needle 36. Preferably, it is believed desirable to have ports spaced around the full circumference of the needle, to provide for an even dispensing and dispersing of alcohol.

Needle 44, illustrated in FIG. 4 is a second alternative embodiment of a helical needle corresponding to needle 14, but with the addition of an insulative sleeve 46, which covers the proximal portion of the electrode. Sleeve 46 limits the application of pacing pulses to the distal portion of the needle. Optionally, additional exit ports corresponding to ports 38, 40 and 42 illustrated in FIG. 43 may also be employed in conjunction with needle 44. These additional exit ports may be limited to the exposed, uninsulated portion of needle 44, or may extend along the entire length of needle 44.

Figure 5:
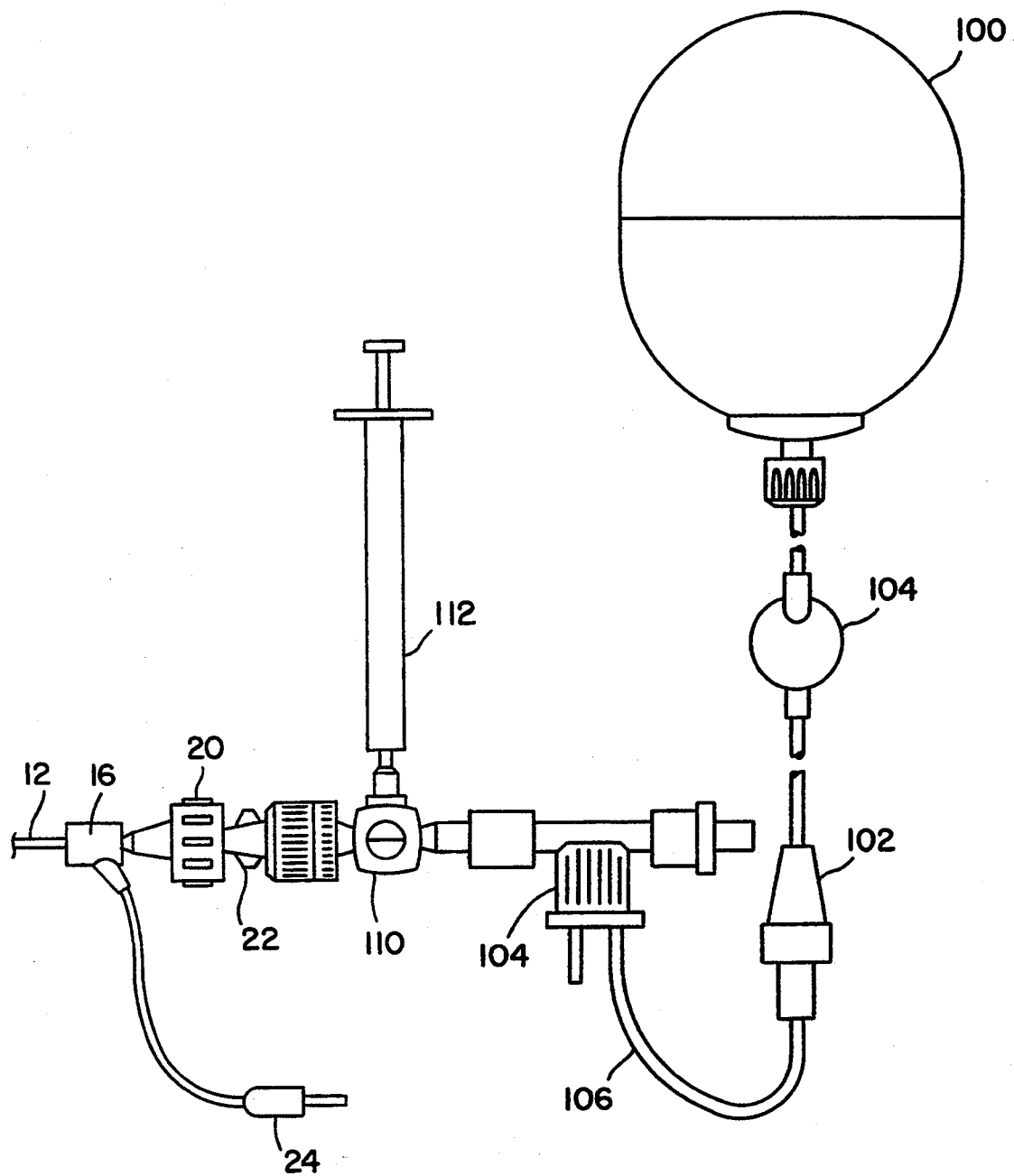
FIG. 5 illustrates the associated apparatus for administration of saline or Ringer's solution before and during application of R-F energy to the helical electrode.

FIG. 5 illustrates a pressurized source for alcohol, exitability reducing agent and Ringer's solution which may be employed in conjunction with catheter illustrated in FIG. 1. Syringe 112 may be coupled to luer lock 22 by means of three way valve 110. Exitability reducing agent alcohol or other ablation fluid is simply placed in the syringe and delivered by injection. In the event that delivery of Ringer's solution is desired to maintain patency of the lumen of the inner tube, the illustrated apparatus also provides for this function. A reservoir 100 is provided, which is commercially manufactured by Block Medical, Inc., and sold under the brand name "Home Pump". The reservoir contains Ringer's solution and provides Ringer's solution at one atmosphere pressure to flow control 102, via filter 104. Flow control 102 may, for example, provide a flow limit of 20 drops or 1 cc per minute. Flow control 102 is coupled to a second flow control element 104, which, in the experimental apparatus employed by the inventors allows for additional adjustability of flow rates. Flow control 104 may be coupled to the luer lock 22 by means of three way valve 110. All other labeled elements correspond to those illustrated in FIG. 1.

While the embodiment illustrated above requires a second element (e.g. a guide catheter or guide wire) for advancing and positioning the catheter at its desired location, it is anticipated that the basic apparatus disclosed above may also be incorporated into catheters which themselves are steerable or deflectable, similar to R-F ablation catheters presently in clinical investigation. Similarly, it is anticipated that in commercial embodiments, alternative mechanisms (e.g. precision pumps) for controlling the flow of anesthetic, alcohol or Ringer's solution may be employed. Similarly, while the inventors have employed alcohol as an ablation solution, other alternative fluids (e.g. formaldehyde) may be workable as well. As such, the embodiment discussed above should be considered exemplary, rather than limiting, in conjunction with the following claims.

In conjunction with the above specification, we claim:

1. An ablation catheter system, comprising:
   an elongated catheter body having a proximal end, a distal end and an internal longitudinal lumen;
   a hollow helical needle mounted to the proximal end of said catheter body and having an internal lumen coupled to the internal lumen of said catheter body; and
   ablation fluid delivery means coupled to the internal lumen of said catheter body for delivering an ablation fluid under pressure to said internal lumen of said catheter body.

2. A catheter system according to claim 1 wherein said ablation fluid delivery means comprises means for delivering alcohol.

3. A catheter system according to claim 1 wherein said ablation fluid delivery means comprises a syringe.

4. A catheter system according to claim 1 wherein said catheter body comprises a torque transfer cable, extending longitudinally along said catheter body.

5. A catheter system according to claim 1 wherein said hollow needle is conductive, wherein said catheter body comprises a longitudinally extending electrical conductor coupled to said hollow needle, and further comprising an electrical connector mounted to said catheter body and coupled to said electrical conductor.

6. A catheter system according to claim 5 wherein said catheter body comprises a conductive torque transfer cable, extending longitudinally along said catheter body, coupled to said hollow needle and to said electrical connector.

7. A catheter system according to claim 5 wherein said catheter body comprises a conductive tube, extending longitudinally along said catheter body, coupled to said hollow needle and to said electrical connector.

8. A catheter system according to claim 1 wherein said catheter body comprises a plastic tube, extending longitudinally along said catheter body, coupled to said hollow needle and to said ablation fluid delivery means.

9. A catheter system according to claim 8, further comprising means for delivering a second fluid to said lumen of said catheter body.

10. A catheter system according to claim 9, wherein said means for delivering a second fluid comprises means for delivering Ringer's solution.

11. A method of catheter ablation, comprising:
    advancing an elongated catheter having a proximal end, a distal end, an internal longitudinal lumen and a helical needle having an internal longitudinal lumen mounted to the proximal end of said catheter with the internal lumen of said needle coupled to the internal lumen of said catheter, to a desired site within a heart;
    screwing said helical needle into heart tissue at said desired site; and
    delivering ablation fluid through the internal lumen of said catheter to said hollow needle under pressure.

12. A method according to claim 11 wherein said step of delivering said ablation fluid comprises delivering alcohol.

13. A method according to claim 11 wherein said step of screwing said helical needle into heart tissue comprises rotating said catheter.

14. A method of catheter ablation, comprising:
    advancing an elongated catheter having a proximal end a distal end, an internal longitudinal lumen and a hollow helical needle mounted to the proximal end of said catheter and coupled to the internal lumen of said catheter to a desired site within a heart;
    screwing said helical needle into heart tissue at said desired site: and
    delivering ablation fluid through the internal lumen of said catheter to said hollow needle under pressure wherein said hollow needle is conductive, wherein said catheter comprises a longitudinally extending electrical conductor coupled to said hollow needle, and further comprising the step of connecting said electrical conductor to ECG monitoring apparatus.

15. A method according to claim 11 wherein said catheter comprises a torque transfer cable, extending longitudinally along said catheter and coupled to said hollow needle and wherein said step of screwing said helical needle into heart tissue comprises rotating said torque transfer cable.

16. A method according to claim 11 wherein said catheter comprises a plastic tube, extending longitudinally along said catheter body, coupled to said hollow needle and further comprising the step of delivering a second fluid through said plastic tube prior to said step of delivering said ablation fluid.

17. A method according to claim 16, wherein said step of delivering a second fluid comprises delivering Ringer's solution.

18. A method of determining a proper location for cardiac ablation, comprising:
    advancing an elongated catheter having a proximal end, a distal end, an internal longitudinal lumen and a hollow needle mounted to the proximal end of said catheter body and coupled to the internal lumen of said catheter to a desired site within a heart;

inserting said needle into heart tissue at said desired site; and delivering an excitability reducing agent in fluid form through the internal lumen of said catheter to said hollow needle; and monitoring the response of said tissue to said agent.

19. A method according to claim 18 wherein said step of delivering said agent comprises delivering lidocaine.

20. A method according to claim 18 wherein said step of delivering said agent comprises delivering esmolol.

21. A method according to claim 18 wherein said hollow needle is a helical needle and wherein said step of inserting said needle into heart tissue comprises rotating said catheter.

22. A method according to claim 18 wherein said hollow needle is conductive, wherein said catheter comprises a longitudinally extending electrical conductor coupled to said hollow needle, and wherein said monitoring step comprises connecting said electrical conductor to ECG monitoring apparatus.

23. A method according to claim 18 wherein said catheter comprises a plastic tube, extending longitudinally along said catheter body, coupled to said hollow needle and further comprising the step of delivering a second fluid through said plastic tube prior to said step of delivering said excitability reducing agent.

24. A method according to claim 23, wherein said step of delivering a second fluid comprises delivering Ringer's solution.

25. A method according to claim 18, further comprising the step of performing cardiac ablation at said desired site following said monitoring step.

26. A method according to claim 18, further comprising the step of repositioning said catheter at a second site following said monitoring step.

27. A method according to claim 18, further comprising the step of determining the amount of said excitability reducing agent required to terminate a heart arrhythmia.

28. A method according to claim 27, further comprising the steps of delivering an ablation fluid to said site as a function of said required amount of said excitability reducing agent.

29. A method according to claim 27, further comprising the steps of relocating said catheter as a function of said required amount of said excitability reducing agent.

* * * * *